United States Patent [19]

Pouletty et al.

[11] Patent Number: 5,256,543
[45] Date of Patent: Oct. 26, 1993

[54] HLA TYPING

[75] Inventors: Philippe Pouletty, Atherton; Peter Chun, South San Francisco, both of Calif.

[73] Assignee: Sangstat Medical Corporation, Menlo Park, Calif.

[21] Appl. No.: 698,319

[22] Filed: May 10, 1991

[51] Int. Cl.$^5$ ................ G01N 33/543; G01N 33/577
[52] U.S. Cl. .................... 435/7.94; 422/56; 435/7.24; 435/962; 435/970; 435/975; 436/518; 436/526; 436/530; 436/531; 436/536; 436/548; 436/809; 436/824; 436/825
[58] Field of Search ............... 435/7.24, 7.4, 7.94, 435/962, 970, 975; 436/518, 526, 530, 531, 536, 548, 809, 817, 824, 825; 422/56

[56] References Cited

U.S. PATENT DOCUMENTS

| | | | |
|---|---|---|---|
| 4,540,659 | 9/1985 | Litman et al. | 435/7 |
| 4,554,088 | 11/1985 | Whitehead et al. | 252/62.54 |
| 4,632,901 | 12/1986 | Valkirs et al. | 435/5 |
| 4,722,899 | 2/1988 | Hamaoka et al. | 435/172.2 |
| 4,725,556 | 2/1988 | Mareschal et al. | 436/500 |
| 4,737,456 | 4/1988 | Weng et al. | 435/7 |
| 4,794,090 | 12/1988 | Parham et al. | 436/531 |
| 4,895,706 | 1/1990 | Root et al. | 422/102 |
| 4,912,034 | 3/1990 | Kalra et al. | 435/7 |
| 4,916,056 | 4/1990 | Brown, III et al. | 435/7 |
| 4,937,199 | 6/1990 | Griffiths | 436/571 |
| 5,006,464 | 4/1991 | Chu et al. | 435/7.1 |
| 5,059,522 | 10/1991 | Wayne | 435/7.2 |
| 5,059,524 | 10/1991 | McKenzie et al. | 435/7.24 |

OTHER PUBLICATIONS

Albrecht, J. and Muller, H., Clin. Chem, (1987), 33:1618–1623. HLA-B27 Typing by Use of Cytofluorometry.

Trapani, J., et al., Immul. Cell Biol. (1988), 66:215–219. Immunoradiometric Assay for the rapid detection of HLA-B27.

Wu, D. Y., et al. DNA, (1989), 8:135–142. Direct Analysis of Single Nucleotide Variation in Human DNA and RNA using in situ Hybridization.

Villar, L., et al., Eur. J. Immunol., (1989), 19:1835–1839. Detection of Soluble Class I Molecules in Serum, Spleen Membranes and Lymphocytes in Culture.

Thurau, S. R., et al., Tissue Antigens, (1989), 33–51-1–519. Expression and Immunogenicity of HLA-B27 in High-Transfection Recipient P815: a New Method Hansen, T., and Hannestad, K., Tissue Antigens, (1987), 30:198–203. Simple Rosette Assay for HLA-B27 Typing of Whole Blood Samples.

Doxiadis, I. and Grosse-Wilde, H., Vox Sang, (1989), 30:198–199. Typing for HLA Class I Gene Products by Using Plasma as Source.

Hill, A., et al., Lancet, (1991), 37:640–642. HLA Class I Typing by PCR: HLA-B27 and an African B27 Subtype.

Davies, H., et al., Transplantation, (1989), 47:524–527. Soluble HLA Antigens in the circulation of Liver Graft Recipients.

Ferreira, A. et al, Clin. Chem. Acta, (1988), 174:207–212. Quantification of Soluble Serum HLA Class I Antigens in Healthy Volunteers and AIDS Patients.

Sakaguchi, K. et al. Hum. Imm. (1988), 21:93–207. Anti--HLA-B7, B27, Bw42, Bw54, Bw55, Bw56, Bw67, Bw73 Monoclonal Antibodies:Specificity, Idiotypes, and Application for.

Thorsby, E., et al., Tissue Antigens, (1983), 21:148–158. HLA-D Restriction of Antigen Specific Proliferative T Cell Responses.

*Primary Examiner*—David Saunders
*Attorney, Agent, or Firm*—Bertram I. Rowland

[57] ABSTRACT

Physiological samples are typed for HLA-B27 by contacting the sample with an antibody which binds to HLA-B7 and is not cross-reactive between HLA-B7 and B27, separating the sample from any complexes which are formed, and then testing the sample for the presence of HLA-B27 with an antibody which is cross-reactive for HLA-B7 and B27 in a STAT test. Particularly, an enzyme conjugate is used which binds to a membrane allowing for the detection of any HLA-B27 bound to the membrane.

17 Claims, No Drawings

HLA TYPING

TECHNICAL FIELD

The technical field of this invention is HLA typing.

BACKGROUND

There is substantial interest in being able to type human leukocyte antigens (HLAs) for a variety of reasons. In many situations it has been found that specific HLA alleles may be associated with a susceptibility to a particular disease. For example, HLA-B27 has been associated with ankylosing spondylitis and related diseases. When transplanting organs to a host it is desirable that the organs be matched, so as to minimize the risk of rejection. HLA typing may also find application in determining lineage, epidemiology and the like.

There is an extensive family of HLA antigens divided into Class I and Class II. In each of the classes, there are polymorphic regions. These sites may or may not provide for epitopes which will induce an immune response which will allow for the preparation of antisera or monoclonal antibodies which are specific for a specific HLA allele and able to distinguish that HLA allele from other HLA allele.

This situation is exemplified by the cross-reactivity between HLA-B27 and HLA-B7 where monoclonal antibodies are not readily available which are specific for HLA-B27, so as not to cross-react with HLA-B7 or other HLA allele.

Since mammals are diploid, there will be pairs of HLA antigens as to each of the particular groups. Thus, unless one can determine specifically a particular HLA allele, one cannot be certain whether there are two different alleles or one is observing cross-reactivity. There is, therefore, substantial interest in developing methods which will allow for the accurate detection of a particular HLA allele, where substantial cross-reactivity is observed with other HLA alleles

RELEVANT LITERATURE

Sakaguchi et al., Human Immunology, 21:193-207 (1988) describes use of monoclonal antibodies in determination of HLA-B27 and a double determinant immunoassay for detection of HLA-B27. Villar et al., Eur. J. Immunol. 19:1835-39 (1989) describe the detection of Class I molecules from a variety of sources. Doxiadis and Grosse-Wilde, Vox Sang 56:196-99 (1989) describe the detection of HLA Class I proteins. Ferreira et al., Clin. Chim. Acta. 174:207-11 (1988) describe the use of a solid-phase enzyme immunoassay for detection of HLA Class I antigens in sera.

SUMMARY OF THE INVENTION

A simple rapid methodology for accurate detection of polymorphic proteins is provided where receptors are not available which distinguish between the two proteins. For example, antibodies do not readily distinguish between HLA-B7 and HLA-B27. HLA-B27 is detected by removing HLA-B7 using monoclonal antibodies reacting with HLA-B7, but not HLA B27 and assaying the eluate for HLA-B27 with a high affinity monoclonal antibody specific for HLA-B7 and -B27.

DESCRIPTION OF THE SPECIFIC EMBODIMENTS

Methods and compositions are provided for the accurate detection of one of two polymorphic antigens in a sample, where the antigens are characterized by having no useful receptor to distinguish between the two antigens, the antigens are members of a much larger group of antigens, usually substantially in excess of 10, where there is substantial cross-reactivity between the antigens in sharing numerous epitopes, and differences between the antigens may be subtle, involving only one or a few amino acids. Exemplary of this situation is the detection of HLA-B27 where the subject invention provides a simple and efficient way, particularly without requiring special equipment for carrying out the process or detecting the result. The method employs as a first stage, using a binding moiety, usually a monoclonal antibody, to specifically deplete HLA-B7 antigen from a sample to a non-interfering level, particularly a blood sample or sample derive therefrom. The resulting HLA-B7 depleted medium is then combined with a second binding moiety, usually a monoclonal antibody, which has a high affinity for B27 and B7. Formation of immune complexes between the binding moiety and any B27 present is detected as indicating the presence of soluble B27 in the sample.

Any binding moiety binding to the target antigen(s) or having the requisite discrimination as to the different HLA alleles may be used. Binding moieties include antibodies, any of the isotypes, e.g., IgG, IgM, etc., fragments thereof, e.g., Fab, F(ab')$_2$, Fv, etc., binding peptides, T-cell receptors, or the like. For the most part, monoclonal antibodies are the most convenient and exemplify the problem of cross-reactivity, where the available monoclonal antibodies in relation to HLA-B27 are unable to specifically distinguish this allele from other alleles. It is understood that in referring to monoclonal antibodies, other binding moieties having analogous cross-reactivities may be substituted.

In the first step, the sample, normally blood, serum, plasma or urine, may be subjected to prior treatment such as dilution in buffered medium, concentration, filtration, or other gross treatment which will not involve any specific separation. The sample can be relatively small, generally being not less than about 1 $\mu$l and will generally not exceed about 500 $\mu$l, generally being in the range of about 10 to 200 $\mu$l. Dilution will usually not be more than 5-fold, more usually not more than 2-fold and concentration will normally not be necessary.

The sample is then contacted with an antibody which is reactive with HLA-B7, but not significantly reactive with HLA-B27, but may be cross-reactive with any other HLA allele. The significant factor for the antibody is that it can distinguish between HLA-B7 and HLA-B27. While many antibodies which ostensibly have this capability, may not prove to be satisfactory, there are a number of antibodies in the ATCC catalogue, as well as catalogues of other repositories, which are satisfactory. As appropriate, purified polyclonal antisera may be employed, where the antisera is prepared in response to HLA-B7 and then purified to ensure that any antibodies cross-reactive between HLA-B7 and HLA-B27 are removed. This can be achieved by passing the antisera through an affinity column comprising HLA-B27 randomly attached to a support, such as agarose, Sephadex, polystyrene beads, magnetic beads, nylon membranes or the like. The eluent may then be assayed for its ability to bind to soluble HLA-B27.

The sample may be passed through an affinity column comprising anti-HLA-B7 bound to a support, may be mixed with anti-HLA-B7, directly or indirectly, covalently or non-covalently bound to beads or particles, e.g., magnetic particles, may be mixed with anti-HLA-B7 and contacted with, either in a column, microtiter well, or other container, anti-mouse Ig antibody bound to a support, or may be mixed with anti-HLA-B7, conjugated with a ligand, e.g., biotin, followed by contacting with avidin, or streptavidin ("strept/avidin") bound to a support as described above. (By "directly or indirectly" is intended that the molecule in question e.g., anti-HLA-B7, is either directly bound to the solid support e.g., covalently through a spacer arm or is bound to an intermediate molecule directly bound to the solid support, e.g., an antibody to the molecule in question.) In each situation, the mixture is contacted or incubated for sufficient time with sufficient amount of the anti-HLA-B7 to provide for substantial complex formation of the anti-HLA-B7 and separation of the HLA-B7-anti-HLA-B7 complex from the sample medium.

Of particular interest is the use of an affinity column employing a receptor bound to a support, conveniently a polysaccharide, more particularly Sepharose. The Sepharose may be activated by any convenient means, such as cyanogen bromide, carbodiimide, bromoacetyl, p-carboxyphenacylbromide, or the like. The receptor may then be conjugated to the support in accordance with conventional ways, depending upon the nature of the functionality bound to the support. Cyanogen bromide and other active halides do not require any activation, while carboxyl groups may be activated with carbodiimide. After reacting the activated support with the antibody, any unreacted functionalities may be terminated with an alkanolamine, e.g., ethanolamine. The amount of antibody will generally be from about 0.2-2 mg/0.5 ml of packed gel.

Alternatively, 1-5 $\mu$ magnetic beads coated with anti-HLA-B7 antibody ($10^{6-107}$ beads) are incubated with a serum specimen e.g., 100 $\mu$l, for 5-30 min at ambient conditions. The beads may be separated using a magnetic filter, a solenoid or the like.

Once the sample has been at least substantially depleted of any HLA-B7 which may have been present, the sample may now be assayed for the presence of B27. Various assays may be employed for detection of the presence of HLA-B27. A number of STAT assay protocols may be employed, as desired. Of particular interest is the use of a STAT test cartridge as described in U.S. application Ser. No. 644,941 filed Jan. 23, 1991 now U.S. Pat. No. 5,147,780.This assay employs a porous filter having measuring regions which are separated by nonporous regions. The filter or membrane is supported by an absorbent layer, which serves to absorb the sample and provides for flow of the sample through the membrane. Desirably, the membrane and absorbent layer are separated by a flow control layer, which may assume various characteristics. Depending upon the nature of the membrane, the membrane may be coated on the fluid exiting side with a coating which will substantially reduce the pore size of the membrane.

Various membranes may be employed, although it is found that glass fiber membranes and nylon membranes appear to be substantially superior to other types of membranes. Conveniently, the glass membrane may be sprayed with an acrylic polymer, which does not interfere with the assay procedure, but provides for the desired flow rate. The amount of acrylic polymer which is applied may be determined empirically, although generally the amount will be in the range of about 0.1 to 1 mg/cm² with a glass membrane having a pore size in the range of about 0.2 to 5$\mu$. The separation of the various measurement regions may be achieved by using non-porous tape or other convenient barrier. In addition, strips may be provided over the barrier to provide a visual indication of the areas in the different regions.

For each sample, there will be desirably three regions: (1) a procedural positive region coated with an anti-immunoglobulin antibody specific for the antibody conjugate which binds to the HLA-B27 or coated with an anti-Ig where the Ig is of the isotype of the anti-HLA-B27; (2) a test region coated with a monoclonal antibody which is cross-reactive with HLA-B27 and HLA-B7, but not cross-reactive with other HLAs; and (3) a negative procedural region coated with the same anti-HLA-B7 monoclonal antibody as used for depleting HLA-B7. A specimen which is HLA-B27 positive shows color development in the first two wells but not the third; a specimen which is HLA-B7 positive and HLA-B27 negative, where the HLA-B7 has been properly depleted or a HLA-B7/B27 negative specimen, would only show a positive result in the first region; and a specimen which is B7 positive and has not been properly absorbed will be positive in all three regions.

The manner in which the presence of HLA-B27 is determined is not critical to this invention. For example, enzyme conjugated antibody cross-reactive with HLA-B7 and HLA-B27, e.g., anti-$\beta_2$-microglobulin antibody or anti-HLA heavy chain monomorphic antibody, may be added after washing the membrane with a convenient wash solution, e.g., a buffered aqueous medium, such as PBS. Various enzymes are available which allow for production of color upon addition of a substrate. Enzymes which have found extensive use include horseradish peroxidase, alkaline phosphatase, glucose-6-phosphate dehydrogenase, $\beta$-galactosidase, glucose oxidase, urease combinations thereof, or the like. Each of these enzymes have been used commercially and numerous substrates are reported which provide for intense color formation. Other methods of detection using radioisotopes, fluorochromes, dyed beads, chemiluminescence and the like, may find use.

The solution containing the enzyme conjugate is added to the STAT test cartridge to provide for binding to any HLA-B27 present. While one can use two steps, where one first adds anti-HLA-B27, followed by antiantibody, there will usually be no advantage in adding this additional step, so that as a practical matter the two-step addition will not be used. After adding the conjugate, the membrane will be washed with an appropriate wash solution, see above, to remove any non-specifically bound conjugate, followed by addition of the development solution containing the substrate and any additional factors which may be required. After sufficient time, one may observe the presence or absence of color, particularly by comparing the various regions, so that one can determine whether the sample is HLA-B27 positive or negative.

The following examples are offered by way of illustration and not by way of limitation.

EXPERIMENTAL

Example 1

HLA B27 test.

1. To 100 $\mu$l of patient serum add 1-4 $\mu$l of 0.5 mg/ml anti-B7 antibody which crossreacts with HLA-B7 and HLA-B40, but does not react with HLA-B27 (Incstar Corporation). Vortex and incubate at room temperature for 5-10 minutes.

2. Add 200-600 µl of magnetic beads coated with goat anti-mouse IgG (Advanced Magnetics, Inc., Catalog No. 4340D) to the above mixture. Cap the tube and mix on a rocker at room temperature for 20-30 minutes.

3. Place the tube on the surface of a strong magnet in up-right position for 2-4 minutes to completely bring down all magnetic beads.

4 Transfer 200 µl of the supernatant to the STAT cartridge. (SangStat Medical Corp., Menlo Park, CA). Allow to drain completely. [STAT cartridge containing 3 miniwells (A, B, C) with nylon membrane coated with antibodies at a concentration of 1 mg/mL in 0.1 M PBS pH 7.2. Miniwell A coated with goat antimouse antibody (Jackson Laboratories) diluted 1:50 in normal goat serum. Miniwell B coated with the anti-HLA B7/B27 monoclonal antibody (Clone SV90.1). Miniwell C coated with the HLA B7/B40 specific monoclonal antibody (Incstar Corporation)].

5. Add 200 µl of antibody conjugate (anti-beta-2 microglobulin mouse antibody conjugated to alkaline phosphatase, diluted to 5 µg/mL in 0.1 M PBS pH 7.2 containing 1% casein and 0.1% Tween 20) to the STAT cartridge. Allow to drain completely.

6. Add 1 mL of wash solution (0.1 M PBS pH 7.2 with 0.1% Tween 20) to each cartridge. Allow to drain completely.

7. Add 200 µl of chromogenic substrate (BCIP/NBT substrate solution (SangStat Medical Corporation). Allow to develop for 3 to 4 minutes.

8. Read results.

INTERPRETATION OF TEST RESULTS

The development of blue-grey rings in the first miniwell only (miniwell A) is a negative test for HLA B27.

The development of blue-grey rings in the first (A) and second (B) miniwells, with the third (C) miniwell showing no rings or lighter rings than in the second (B) miniwell, is a positive test for HLA B27.

QUALITY CONTROL

If there is no color development in the first miniwell (Miniwell A, positive procedural reference) or uniform color development in all miniwells, the test is invalid.

Color development in miniwell C indicates that removal of HLA B7 (or B40) was incomplete or that there is an interference which may be related to anti-mouse IgG antibodies in the serum specimen.

RESULTS 30 specimens collected from individuals previously phenotyped by microcytotoxicity assay were tested by the rapid assay (HLA B27).

| HLA B27 STAT | CYTOTOXICITY | | | |
|---|---|---|---|---|
| | B27+/B7+ | B27+/B7− | B27−/B7+ | B27−/B7− |
| Positive | 4 | 10 | 0 | 0 |
| Negative | 0 | 0 | 5 | 15 |
| Invalid | 0 | 0 | 1 | 0 |

A preferred embodiment is to have the immunoglobulins as one or more circles, where there is a concentration gradient from the center outward. Particularly desirable is to have a relatively high immunoglobulin concentration central region and a substantially lower concentration outer periphery. This embodiment is described in U.S. application Ser. No. 644,941 filed Jan.23, 1991 now U.S. Pat. No. 5,147,780. The concentration gradient can be readily achieved by using a porous pointed stub which is pressed against the membrane, so that a significant proportion of the immunoglobulin present in the sample becomes bound around the stub point creating a relatively high concentration in a central region and a substantially lower concentration around the central region.

The rate of flow of the sample through the membrane will provide for at least about 10 to 120 sec for contact of the sample with the antibody on the membrane. Similarly, the rate of flow and volume of the enzyme conjugate will allow for 10 to 120 sec of contact with the enzyme conjugate in the various regions. Finally, the rate of flow and volume of the substrate will allow for 10 to 120 sec of reaction of the enzyme with the substrate.

Conveniently, kits may be provided comprising a STAT test cartridge having the three regions described above, the packing for the column, the enzyme conjugate, and, as appropriate, other reagents such as wash solutions, enzyme substrate, and the like.

It is evident from the above results, that the subject procedure provides for a simple effective method to accurately determine the B27 HLA type of an individual, without interference from other HLAs. Thus, a rapid diagnosis may be made of an individual's propensity to certain diseases. The procedure is simple, does not require sophisticated equipment for performance or measurement and can be easily carried out by unsophisticated operators.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the presence of a first soluble antigen in a physilogical sample in the potential presence of a second antigen, where said first and second antigens are characterized by being members of a polymorphic group of antigens which share numerous epitopes and there is no useful receptor which can distinguish between said first and second antigens, said method comprising:

combining said physiological sample with a first binding moiety binding to at least said second antigen, but having substantially no binding affinity to said first antigen and separating said sample from complexes formed with said binding moiety to provide a second antigen depleted sample;

combining said second antigen depleted sample with a second binding moiety cross-reactive with said first and second antigens, but substantially not cross-reactive with other antigens of said group, whereby complexes form between any first antigen present and said second binding moiety; and determining the presence of said first antigen by detecting the presence of first antigen complexes with said second binding moiety.

2. A method for determining the presence of soluble HLA-B27 in a physiological sample, said method comprising:

combining said physiological sample with a first binding moiety binding to HLA-B7, but having substantially no binding affinity to HLA-B27 and separating said sample from complexes formed with said binding moiety to provide an HLA-B7 depleted sample;

combining said HLA-B7 depleted sample with a second binding moiety cross-reactive with HLA-B7 an HLA-B27, but substantially not cross-reactive with other HLA, whereby complexes form between HLA-B27 present and said second binding moiety; and determining the presence of said HLA-B27 by detecting the presence of HLA-B27 complexes with said second binding moiety.

3. A method according to claim 2, wherein at least said second binding moiety is a monoclonal antibody.

4. A method according to claim 2 wherein said first binding moiety is bound to a solid support.

5. A method according to claim 4, wherein said solid support is a polysaccharide column packing.

6. A method according to claim 4, wherein said solid support is magnetic beads.

7. A method according to claim 2, wherein said sample is blood, plasma or serum.

8. A method according to claim 2, wherein said sample is urine.

9. A method for determining the presence of soluble HLA-B27 in a physiological sample, said method comprising:

incubating said sample, a first antibody binding to HLA-B7, but having substantially no binding affinity to HLA-B27, and magnetic beads, wherein said first antibody is bound or becomes bound to said magnetic beads, whereby HLA-B7 becomes bound to said magnetic beads;

separating said magnetic beads to provide a HLA-B7 depleted sample;

combining said HLA-B7 depleted sample with an assay system comprising a membrane having three regions: a first region to which is bound a second antibody cross-reactive with HLA-B7 and HLA-B27, but substantially not cross-reactive with other HLA; a second region to which is bound said first antibody; and a third region to which is bound antibody to an antibody conjugate comprising an antibody to Class I HLA and a label capable of providing a detectable signal;

determining by means of said antibody conjugate the presence of complex formation of said HLA-B7 and -B27 with said antibodies bound to said membrane, whereby a positive result in said first and third regions and a negative result in said second region indicates the presence of HLA-B27 in said sample.

10. A method according to claim 9, wherein at least said second antibody is a monoclonal antibody.

11. A method according to claim 9, wherein said membrane is a nylon membrane.

12. A method according to claim 9, wherein said label is enzyme.

13. A membrane comprising at least two regions: a first region to which is bound a first antibody cross-reactive with HLA-B7 and HLA-B27, but substantially not cross-reactive with other HLA antigens; a second region to which is bound a second antibody reactive with HLA-B7, but not HLA-B27.

14. A membrane according to claim 13, wherein said membrane is a nylon membrane.

15. A membrane according to claim 14, wherein said membrane is coated with acrylic polymer to control the flow rate.

16. A membrane comprising at least two regions: a first region to which is bound a first antibody cross-reactive with first and second antigens, but substantially not cross-reactive with other antigens of a group; a second region to which is bound a second antibody reactive with said second antigen, but not said first antigen, wherein said antigens and said group are characterized by being members of a polymorphic group of antigens which share numerous epitopes and there is no useful receptor which can distinguish between said first and second antigens.

17. A kit comprising the membrane according to claim 13 and an enzyme conjugate of an anti-monomorphic antibody reactive with HLA-B7 and HLA-B27.

* * * * *